United States Patent
Sasaki et al.

(10) Patent No.: US 6,365,610 B1
(45) Date of Patent: Apr. 2, 2002

(54) OZONIDE COMPOUNDS WITH INHIBITORY ACTIVITY FOR UROKINASE PRODUCTION AND ANGIOGENESIS

(75) Inventors: Takuma Sasaki, Kanazawa; Masatomo Nojima, Toyonaka, both of (JP)

(73) Assignee: Taiho Pharmaceutical Company Ltd., Tokyo (JP)

( * ) Notice: Subject to any disclaimer, the term of this patent is extended or adjusted under 35 U.S.C. 154(b) by 0 days.

(21) Appl. No.: 09/508,674

(22) PCT Filed: Jul. 28, 1999

(86) PCT No.: PCT/JP99/04030

§ 371 Date: Mar. 28, 2000

§ 102(e) Date: Mar. 28, 2000

(87) PCT Pub. No.: WO00/06154

PCT Pub. Date: Feb. 10, 2000

(30) Foreign Application Priority Data

Jul. 29, 1998 (JP) .............................. 10-230262

(51) Int. Cl.[7] ........................ A61K 31/35; A61K 31/41; C07D 493/08; C07D 498/08
(52) U.S. Cl. ................. 514/359; 514/229.5; 514/229.8; 514/543; 514/544; 514/452; 544/65; 548/131; 548/218; 549/358; 549/360; 549/383; 549/387
(58) Field of Search ............................ 514/229.5, 229.8, 514/453, 454, 359, 452; 548/218, 131; 549/358, 360, 383, 387; 544/65

(56) References Cited

PUBLICATIONS

English Abstract of JP–A–63–122,687—Otake et al. (1988).
J. Org. Chem., 1993, vol. 58, No. 1, pp. 135 to 141.
J. Org. Chem., 1990, vol. 55, No. 13, pp. 4221 to 4222.

*Primary Examiner*—Floyd D. Higel
(74) *Attorney, Agent, or Firm*—Arent Fox Kintner Plotkin Kahn

(57) ABSTRACT

The invention provides a urokinase production inhibitor or angiogenesis inhibitor comprising as an active component an ozonide derivative represented by the formula (1), and method of prevention or therapy using the inhibitor (1)

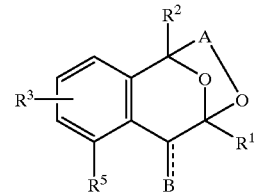

wherein A is an oxygen atom or N—R (wherein R is phenyl or phenyl having as a substituent lower alkyl having 1 to 6 carbon atoms, lower alkoxyl having 1 to 6 carbon atoms or a halogen atom); B is an oxo group or —$R^4$; and (1) when A is an oxygen atom, $R^1$ is a hydrogen atom, etc., $R^2$ is phenyl, etc., $R^3$ is a hydrogen atom, etc., B is an oxo group or —$R^4$, $R^4$ is a hydrogen atom, etc., $R^5$ is a hydrogen atom, etc.; (2) when A is N—R, $R^1$ is a hydrogen atom, etc., $R^2$ is a hydrogen atom, etc., $R^3$ is a hydrogen atom, etc., B is —$R^4$, $R^4$ is a hydrogen atom, etc., $R^5$ is a hydrogen atom, etc.

16 Claims, No Drawings

OZONIDE COMPOUNDS WITH INHIBITORY ACTIVITY FOR UROKINASE PRODUCTION AND ANGIOGENESIS

This application is a 371 of PCT/JP99/04030 filed Jul. 28, 1999.

TECHNICAL FIELD

The present invention relates to novel urokinase production inhibitors, angiogenesis inhibitors and a preventive or therapeutic method with use of the inhibitor.

BACKGROUND ART

Urokinase (urine-type plasminogen activator, i.e., uPA) is a protease which is highly specific to a single peptide linkage in plasminogen. Urokinase converts plasminogen to plasmin which is an active fibrinolytic enzyme. Activated plasmin acts on fibrin, fibronectin and laminin, converts inactive matrix metalloprotease (MMP) to active MMP and promotes liquefaction of collagen, a component of the basement membrane. In addition to the function of a protease, urokinase also has activity to promote the migration of vascular endothelial cells and to promote tube formation on Matrigel, serving an important function in angiogenesis.

The physiological processes in which urokinase participates include, for example, angiogenesis, osteoanagenesis, nidation, infiltration of immunocytes into inflammatory sites, ovulation, spermatogenesis, anagenesis for the repair of wounds and differentiation of organs, local infiltration of fibrosis and tumor into adjacent regions, metastatic spread of tumor cells from the primary site to a secondary site, and disorganization in arthritis. Accordingly urokinase inhibitors have activities against angiogenesis, arthritis, inflammation, invasion, metastasis, osteoporosis and retinopathy (angiogenesis-dependent retinopathy), contraceptive activity and activity to inhibit growth of tumor. It is therefore expected to develop medicinals which will act on urokinase as a molecular target. Reports are made on useful effects of anti-urokinase monoclonal antibodies and some urokinase inhibitors. For example, it is reported that anti-urokinase monoclonal antibodies block the invasiveness of tumor cells in vitro [Cancer Res., 51, 3690–3695(1991); Exp. Cell Res., 192, 453–459(1991)]. Reportedly, amiloride, a known urokinase inhibitor having medium efficacy, blocks the metastasis of tumors in vivo [Anticancer Res., 8, 1373–1376 (1988)], and prevents angiogenesis or development of capillary reticular structures in vitro [J. Cell Biol. 115(3 Pt 2):402a(1991)].

The ozonide derivatives according to the present invention include some compounds which are known [for example, J. Am. Chem. Soc. (1984), 106(10), 2932–6, J. Org. Chem. (1985), 50(9), 1504–9, J. Org. Chem. (1990), 55(13), 4221–2, Ann. Chim. (Paris) 9 (7–8), 359–97(1964), J. Am. Chem. Soc. (1983), 105(8), 2414–26, J. Org. Chem. (1993), 58(1), 135–41, J. Org. Chem. (1985), 50(2), 275–7, etc.]. However, the literature relates only to preparation processes and optochemical properties, and nothing has been known about the fact that these compounds have high activity to inhibit production of urokinase and are useful as urokinase production inhibitors and angiogenesis inhibitors.

An object of the present invention is to provide novel urokinase production inhibitors and angiogenesis inhibitors, and a preventive or therapeutic method with use of such an inhibitor.

DISCLOSURE OF THE INVENTION

The present invention provides a urokinase production inhibitor comprising as an active component an ozonide derivative represented by the formula (1)

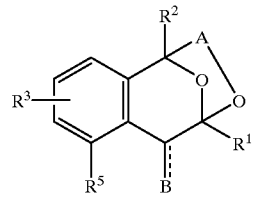

wherein A is an oxygen atom or N—R (wherein R is phenyl or phenyl having as a substituent lower alkyl having 1 to 6 carbon atoms, lower alkoxyl having 1 to 6 carbon atoms or a halogen atom); B is an oxo group or —$R^4$; and (1) when A is an oxygen atom, $R^1$ is a hydrogen atom, lower alkyl having 1 to 6 carbon atoms, phenyl or phenyl having as a substituent lower alkyl having 1 to 6 carbon atoms, lower alkoxyl having 1 to 6 carbon atoms, lower alkoxycarbonyl having 2 to 7 carbon atoms or a halogen atom, $R^2$ is phenyl or phenyl having as a substituent lower alkyl having 1 to 6 carbon atoms, lower alkoxyl having 1 to 6 carbon atoms or a halogen atom, $R^3$ is a hydrogen atom, lower alkyl having 1 to 6 carbon atoms, lower alkoxyl having 1 to 6 carbon atoms or a halogen atom, B is an oxo group or —$R^4$, $R^4$ is a hydrogen atom, lower alkyl having 1 to 6 carbon atoms, a halogen atom, lower alkanoyl having 2 to 6 carbon atoms or phenyl, and $R^5$ is a hydrogen atom, lower alkyl having 1 to 6 carbon atoms, lower alkoxyl having 1 to 6 carbon atoms or a halogen atom or forms an aromatic 6-membered ring when combined with $R^4$; or (2) when A is N—R, $R^1$ is a hydrogen atom, lower alkyl having 1 to 6 carbon atoms, phenyl or phenyl having as a substituent lower alkyl having 1 to 6 carbon atoms, lower alkoxyl having 1 to 6 carbon atoms or a halogen atom, $R^2$ is a hydrogen atom or lower alkyl having 1 to 6 carbon atoms, $R^3$ is a hydrogen atom, lower alkyl having 1 to 6 carbon atoms, lower alkoxyl having 1 to 6 carbon atoms or a halogen atom, B is —$R^4$, $R^4$ is a hydrogen atom, phenyl or phenyl having as a substituent lower alkyl having 1 to 6 carbon atoms, lower alkoxyl having 1 to 6 carbon atoms or a halogen atom, and $R^5$ is a hydrogen atom, lower alkyl having 1 to 6 carbon atoms, lower alkoxyl having 1 to 6 carbon atoms or a halogen atom or forms an aromatic 6-membered ring when combined with $R^4$.

The invention further provides a urokinase production inhibitor composition containing an ozonide derivative represented by the formula (1) and a pharmacologically acceptable carrier.

The invention further proposes use of an ozonide derivative represented by the formula (1) for preparing a urokinase production inhibitor.

The invention further provides a method of inhibiting production of urokinase by administering to a human an effective amount of an ozonide derivative represented by the formula (1).

The invention further provides an angiogenesis inhibitor comprising as an active component an ozonide derivative represented by the formula (1).

The invention further provides an angiogenesis inhibitor composition containing an ozonide derivative represented by the formula (1) and a pharmacologically acceptable carrier.

The invention further proposes use of an ozonide derivative represented by the formula (1) for preparing an angiogenesis inhibitor.

The invention further provides a method of preventing or treating a disease accompanying angiogenesis by administering to a human an effective amount of an ozonide derivative represented by the formula (1).

The invention further provides an agent for preventing or treating a malignant tumor comprising as an active component an ozonide derivative represented by the formula (1).

The invention further provides a composition for preventing or treating a malignant tumor containing an ozonide derivative represented by the formula (1) and a pharmacologically acceptable carrier.

The invention further proposes use of an ozonide derivative represented by the formula (1) for preparing an agent for preventing or treating a malignant tumor.

The invention further provides a method of preventing or treating a malignant tumor by administering to a human an effective amount of an ozonide derivative represented by the formula (1).

The invention further provides an agent for preventing or treating metastasis of a tumor comprising as an active component an ozonide derivative represented by the formula (1).

The invention further provides a composition for preventing or treating metastasis of a tumor containing an ozonide derivative represented by the formula (1) and a pharmacologically acceptable carrier.

The invention further proposes use of an ozonide derivative represented by the formula (1) for preparing an agent for preventing or treating metastasis of a tumor.

The invention further provides a method of preventing or treating metastasis of a tumor by administering to a human an effective amount of an ozonide derivative represented by the formula (1).

The compounds serving as the active component of the invention and represented by the formula (1) have the following basic structures (A) to (D).

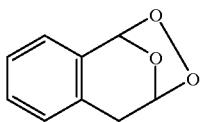
(A)

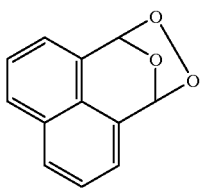
(B)

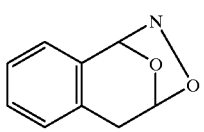
(C)

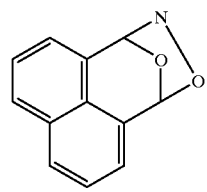
(D)

According to the invention, the group B included in the formula (1) is an oxo group or a group represented by $-R^4$, and the group B is combined with a ring by a single bond or double bond. When B is the group $-R^4$, this group can be combined with $R^5$ to form an aromatic 6-membered ring.

According to the invention, examples of lower alkyl groups having 1 to 6 carbon atoms are straight-chain or branched lower alkyl groups having 1 to 6 carbon atoms, such as methyl, ethyl, propyl, isopropyl, butyl, sec-butyl, tert-butyl, pentyl and hexyl, among which preferable are those having 1 to 4 carbon atoms, i.e., methyl, ethyl, propyl, isopropyl, butyl, sec-butyl and tert-butyl.

Examples of lower alkoxyl groups having 1 to 6 carbon atoms are straight-chain or branched lower alkoxyl groups having 1 to 6 carbon atoms, such as methoxy, ethoxy, propoxy, isopropoxy, butyloxy, sec-butyloxy, tert-butyloxy, pentyloxy and hexyloxy, among which methoxy and ethoxy are preferable.

Examples of halogen atoms are fluorine atom, chlorine atom, bromine atom and iodine atom.

Examples of lower alkoxycarbonyl groups having 2 to 7 carbon atoms are straight-chain or branched lower alkoxycarbonyl groups having 2 to 7 carbon atoms, such as methoxycarbonyl, ethoxycarbonyl, n-propoxycarbonyl, i-propoxycarbonyl, n-butyloxycarbonyl, sec-butyloxycarbonyl, tert-butyloxycarbonyl, pentyloxycarbonyl and hexyloxycarbonyl, among which methoxycarbonyl and ethoxycarbonyl are preferable.

Examples of lower alkanoyl groups having 2 to 6 carbon atoms are alkanoyl groups having 2 to 6 atoms, such as acetyl, propionyl, butyryl, pentanoyl and hexanoyl, among which acetyl is preferable.

Preferable among the active components represented by the formula (1) of the invention are as follows.

[1] When having the basic structure (A): Preferable are compounds wherein A is an oxygen atom, $R^1$ is a hydrogen atom, methyl, ethyl, phenyl or phenyl having as a substituent methyl, methoxy, methoxycarbonyl or a chlorine atom, $R^2$ is phenyl or phenyl having as a substituent methyl, methoxy or a chlorine atom, $R^3$ is a hydrogen atom, B is oxo group or $-R^4$, $R^4$ is a hydrogen atom, methyl, ethyl, isopropyl, tert-butyl, a chlorine atom, acetyl or phenyl, and $R^5$ is a hydrogen atom. More preferable are compounds wherein A is an oxygen atom, $R^1$ is a hydrogen atom, methyl or phenyl, $R^2$ is phenyl or phenyl having methoxy as a substituent, $R^3$ is a hydrogen atom, $R^4$ is a hydrogen atom, methyl, isopropyl or phenyl, and $R^5$ is a hydrogen atom.

[2] When having the basic structure (B): Preferable are compounds wherein A is an oxygen atom, $R^1$ is a hydrogen atom or phenyl, $R^2$ is phenyl, $R^3$ is a hydrogen atom, and $R^5$ is combined with $R^4$ to form a phenyl ring.

[3] When having the basic structure (C): Preferable are compounds wherein A is N—R, R is phenyl, $R^1$ is a hydrogen atom or phenyl, $R^2$ is a hydrogen atom, $R^3$ is a hydrogen atom, $R^4$ is a hydrogen atom or phenyl, and $R^5$ is a hydrogen atom.

[4] When having the basic structure (D): Preferable are compounds wherein A is N—R, R is phenyl, $R^1$ is a hydrogen atom or phenyl, $R^2$ is a hydrogen atom, $R^3$ is a hydrogen atom, and $R^5$ is combined with $R^4$, forming a phenyl ring.

Due to the presence of asymmetric carbon, optical isomers are present for the compounds represented by the formula (1) and useful as the active components of the invention. The isomers of the respective compounds and mixtures of such isomers are also included in the active components of the invention. Exo-isomers and endo-isomers are also present due to different configurations. While the active components of the invention include these isomers and mixtures thereof, preferable are exo-isomers.

The compounds represented by the formula (1) and serving as the active components of the invention are prepared by substantially the same processes as disclosed, for example, in J. Am. Chem. Soc. (1984), 106(10), 2932–6, J. Org. Chem. (1985), 50(9), 1504–9, J. Org. Chem. (1990), 55(13), 4221–2, Ann. Chim. (Paris) 9 (7–8), 359–97(1964), J. Am. Chem. Soc. (1983), 105(8), 2414–26, J. Org. Chem. (1993), 58(1), 135–41, and J. Org. Chem. (1985), 50(2), 275–7. More specifically, these processes are as follows.

When A is an oxygen atom, compounds represented by the formula (1a) and serving as the active component of the invention are prepared by the following reaction step i.

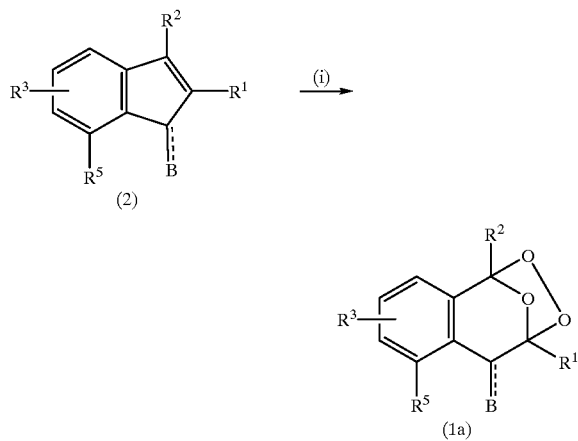

wherein $R^1$ to $R^3$, B and $R^5$ are same as above.
[Reaction Step i]

A compound represented by the formula (2) is reacted with ozone in a suitable solvent, whereby a compound represented by the formula (1a) is obtained. The solvent is not limited specifically insofar as the solvent does not participate in the reaction. Examples of useful solvents are methylene chloride, chloroform, carbon tetrachloride, ether, tetrahydrofuran, benzene and petroleum ether. For the reaction, ozone is used in 0.5 to 5 moles, preferably 1 to 3 moles, per mole of the compound (2). The reaction is conducted usually at a temperature of −10 to 20° C., preferably −5 to 5° C., for 5 to 30 minutes, preferably for 10 to 15 minutes.

The compound represented by the formula (2) is a known compound disclosed in J. Org. Chem., 6, 534(1941), J. Am. Chem. Soc., 56, 1337(1934), ibid., 65, 567(1943), ibid., 106, 2932(1984), Acta Chem. Scand., Ser. B. B28, 295(1974), Helv. Chim. Acta, 30, 1320(1947), etc., or prepared by substantially the same process as disclosed in the literature.

(2) When A is N—R, compounds represented by the formula (1b) and serving as the active component of the invention are repared by the following reaction step ii.

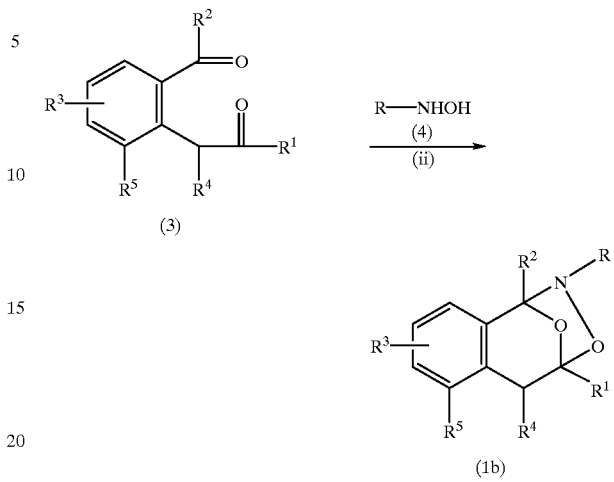

wherein R, $R^1$ to $R^5$ are same as above.
[Reaction Step ii]

A compound represented by the formula (3) is reacted with a compound represented by the formula (4) in a suitable solvent, whereby a compound represented by the formula (1b) is obtained. The solvent is not limited specifically insofar as the solvent does not participate in the reaction. Examples of useful solvents are methanol, ethanol, benzene, ether, tetrahydrofuran, dioxane, methylene chloride, chloroform and carbon tetrachloride. For the reaction, the compound (4) is used in 0.5 to 5 moles, preferably 1 to 3 moles, per mole of the compound (3). The reaction is conducted usually at a temperature of 0 to 50° C., preferably 10 to 30° C., for 1 to 48 hours, preferably for 10 to 24 hours.

Incidentally, the compound represented by the formula (3) can be prepared from the compound represented by the formula (1a) and obtained by the reaction step i, by reducing the compound (1a) with a reducing agent in a suitable solvent. The solvent is not limited specifically insofar as the solvent does not participate in the reaction. Examples of useful solvents are benzene, ether, methylene chloride, chloroform and petroleum ether. Examples of reducing agents usable are triphenylphosphine, trimethyl phosphite, triphenyl phosphite and dimethyl sulfide, among which triphenylphosphine is preferable. For the reaction, the reducing agent is used in 0.5 to 5 moles, preferably 1 to 3 moles, per mole of the compound (1a). The reaction is conducted usually at a temperature of 0 to 50° C., preferably 10 to 30° C., for 1 to 48 hours, preferably for 10 to 24 hours.

The compound (1a) or (1b) obtained by the foregoing reaction step can be easily isolated from the reaction mixture and purified by a usual separation or purifying method such as column chromatography, recrystallization or vacuum distillation.

The active component of the present invention is used usually in the form of usual pharmaceutical preparations. Such preparations are formulated using diluents or excipients which are usually used, such as fillers, extenders, binders, humectants, disintegrators, surfactants and glazing agents. The pharmaceutical preparations can be in various forms each as selected in conformity with the therapeutic purpose. Examples of typical forms are tablets, pills, powders, liquid preparations, suspensions, emulsions, granules, encapulated preparations, suppositories, injections (liquid, suspension, etc.), ointments, etc.

Examples of carriers for use in preparing tablets are excipients such as lactose, sucrose, sodium chloride, glucose, urea, starch, calcium carbonate, kaolin, crystalline cellulose and silicic acid, binders such as water, ethanol, propanol, syrup, glucose solution, starch solution, gelatin solution, carboxymethyl cellulose, shellac, methyl cellulose, potassium phosphate and polyvinylpyrrolidone, disintegrators such as dried starch, sodium alginate, agar powder, laminaria powder, sodium hydrogencarbonate, calcium carbonate, polyoxyethylene sorbitan fatty acid esters, sodium laurylsulfate, stearic acid monoglyceride, starch and lactose, disintegration suppressants such as sucrose, stearic acid, cacao butter and hydrogenated oils, absorption promoters such as quaternary ammonium bases and sodium laurylsulfate, humectants such as glycerin and starch, adsorbents such as starch, lactose, kaolin, bentonite and colloidal silicic acid, glazing agents such as purified talc, stearic acid salts, boric acid powder and polyethylene glycol, etc. When required, the tablets can be those having a usual coating, such as sugar-coated tablets, gelatin-coated tablets, enteric-coated tablets, film-coated tablets, double-layer tablets and multi-layer tablets.

Examples of carriers for use in preparing pills are excipients such as glucose, lactose, starch, cacao butter, hardened vegetable oils, kaolin and talc, binders such as gum arabic powder, tragacanth powder, gelatin and ethanol, disintegrators such as laminaria and agar, etc. Examples of carriers for use in preparing suppositories are polyethylene glycol, cacao butter, higher alcohols, higher alcohol esters, gelatin, semi-synthetic glycerides, etc. Encapsulated preparations are obtained in the usual manner by mixing the compound of the invention with such carriers as exemplified above, and filling the mixture into hard gelatin capsules or soft capsules.

When to be formulated into injections, liquid preparations or suspensions are sterilized and preferably made isotonic with blood. Examples of diluents for use in preparing such preparations are water, aqueous solution of lactic acid, ethyl alcohol, propylene glycol, ethoxylated isostearyl alcohol, polyoxyisostearyl alcohol, polyoxyethylene sorbitan fatty acid ester, etc. The pharmaceutical preparations may have further incorporated therein sodium chloride, glucose or glycerin in an amount sufficient to prepare an isotonic solution. The solution may also contain a usual auxiliary solubilizing agent, buffer, analgesic or the like added thereto. Further when required, the pharmaceutical preparations may have incorporated therein a coloring agent, preservative, perfume, flavoring, sweetener and the like, and other medicinals. Examples of diluents usable for formulating preparations in the form of a paste, cream or gel are white petrolatum, paraffin, glycerin, cellulose derivatives, polyethylene glycol, silicon and bentonite. The amount of the compound of the invention represented by the formula (1) or a salt thereof (active component compound) to be incorporated in the foregoing pharmaceutical preparations is not limited specifically but suitably determined from a wide range. It is usually desirable that the pharmaceutical preparations contain 1 to 70 wt. % of the active component.

The method of administering the pharmaceutical preparation of the invention is not limited specifically but determined according to the form of preparation, age, sex and other conditions of the patient and degree of symptom of the patient. For example, tablets, pills, solutions, suspensions, emulsions, granules and capsules are given orally. Injections are intravenously given singly or as mixed with a usual auxiliary solution such as glucose or amino acid solution. When required, the injection is singly administered intramuscularly, intracutaneously, subcutaneously or intraperitoneally. Suppositories are introduced into the rectum.

The dosage of the active component of the pharmaceutical preparation of the invention is suitably determined according to the mode of administration, age, sex, other conditions and degree of symptom of the patient. The compound of the invention serving as the active component is administered usually at a daily dose of about 1 to about 1000 mg/kg body weight, preferably about 10 to about 100 mg/kg body weight. The preparation can be given once or dividedly up to four times per day.

The medicinal of the invention has high activity to inhibit production of urokinase and is useful as a urokinase production inhibitor.

The medicinal of the invention also has high angiogenesis inhibitory activity and is therefore useful as an agent for treating or preventing diseases accompanying angiogenesis. The diseases accompanying angiogenesis include, for example, malignant tumors, metastases of tumors, benign tumors (e.g., hemangioma, acoustic neurinoma, neurofibroma, trachoma and pyogenic granuloma), vascular dysfunction, inflammation and immune disorders, Behcet's syndrome. gout, arthritis, chronic articular rheumatism, psoriasis, diabetic retinopathy and other diseases originating in ocular blood vessels (e.g., fibroplasia of the posterior lens, macular degeneration, rejection of corneal transplant and angiogenesis glaucoma), osteoporosis, etc. By virtue of the above activity, the medicinal of the invention especially has high activity to inhibit the growth of tumors and to inhibit the metastasis of tumors and is therefore useful as an agent for preventing or treating malignant tumors and as an agent for preventing or treating the metastasis of tumors. Although not limited particularly, examples of malignant tumors are cancer of the head and neck, esophageal cancer, gastric cancer, colon cancer, rectal cancer, liver cancer, gallbladder cancer, bile duct cancer, pancreatic cancer, lung cancer, breast cancer, ovarian cancer, bladder cancer, prostate cancer, testicular tumor, bone and soft part sarcomas, cervical cancer, skin cancer, brain tumor and like solid malignant tumors. Although not limited specifically, metastases of tumors are those of tumors which are sensitive to the therapy of the invention, including, for example, metastases to the liver, lungs and other organs, and metastases to lymph nodes, bones, the brain and other tissues or structures.

BEST MODE OF CARRYING OUT THE INVENTION

The present invention will be described below in greater detail with reference to preparation examples, examples and test examples.

PREPARATION EXAMPLE 1

Preparation of 4,5-dihydro-1,5-diphenyl-4-methyl-1,4-epoxy-1H-2,3-benzodioxepin (Compound 1)

A 282 mg quantity (1 mmol) of 1,3-diphenyl-2-methylindene, a known compound, was reacted with ozone in 1.5 times the molar quantity of the compound in 1.5 ml of methylene chloride at 0° C., the solvent was distilled off in a vacuum, and the residue was thereafter subjected to silica gel column chromatography (eluent: benzene-hexane, 1:5) for separation. Subsequently, recrystallization from methanol gave 198 mg of exo-isomer of the desired compound (yield 60%). The physical properties of the product are shown in Table 1.

PREPARATION EXAMPLE 2

Preparation of 4,5-dihydro-5-methyl-4-phenyl-1-p-tolyl-1,4-epoxy-1H-2,3-benzodioxepin (Compound 2)

A 296 mg quantity (1 mmol) of 1-methyl-2-phenyl-3-p-tolylindene, a known compound, was reacted with ozone in 1.5 times the molar quantity of the compound in 15 ml of methylene chloride at 0° C., and the residue was thereafter subjected to silica gel column chromatography (eluent: benzene-hexane, 1:5) for separation. Recrystallization from methanol gave 240 mg of exo-isomer of the desired compound (yield 70%). The physical properties of the product are shown in Table 1.

PREPARATION EXAMPLE 3
Preparation of 4,5-dihydro-1-p-anisyl-5-methyl-4-phenyl-1,4-epoxy-1H-2,3-benzodioxepin (Compound 3)

A 312 mg quantity (1 mmol) of 1-methyl-2-phenyl-3-p-anisylindene, a known compound, was reacted with ozone in 1.5 times the molar quantity of the compound in 15 ml of methylene chloride at 0° C. The solvent was distilled off, and the residue was thereafter subjected to silica gel column chromatography (eluent: benzene-hexane, 1:5) for separation. Recrystallization from methanol gave 252 mg of exo-isomer of the desired compound (yield 70%). The physical properties of the product are shown in Table 1.

PREPARATION EXAMPLE 4
Preparation of 4,5-dihydro-1,4-diphenyl-5-isopropyl-1,4-epoxy-1H-2,3-benzodioxepin (Compound 4)

A 310 mg quantity (1 mmol) of 1-isopropyl-2,3-diphenylindene, a known compound, was reacted with ozone in 1.5 times the molar quantity of the compound in 20 ml of methylene chloride at 0° C. The solvent was distilled off, and the residue was thereafter subjected to silica gel column chromatography (eluent: benzene-hexane, 1:5) for separation. Recrystallization from methanol gave 251 mg of exo-isomer of the desired compound (yield 70%). The physical properties of the product are shown in Table 1.

PREPARATION EXAMPLE 5
Preparation of 4,5-dihydro-5-tert-butyl-1,4-diphenyl-1,4-epoxy-1H-2,3-benzodioxepin (Compound 5)

A 324 mg quantity (1 mmol) of 1-t-butyl-2,3-diphenylindene, a known compound, was reacted with ozone in 2 times the molar quantity of the compound in 20 ml of methylene chloride at 0° C. The solvent was distilled off, and the residue was thereafter subjected to silica gel column chromatography (eluent: benzene-hexane, 1:5) for separation. Recrystallization from methanol gave 278 mg of exo-isomer of the desired compound (yield 75%). The physical properties of the product are shown in Table 1.

PREPARATION EXAMPLE 6
Preparation of 1-phenyl-1,4-epoxy-1H,4H-naphtho[1,8-de][1,2]dioxepin (Compound 6)

A 228 mg quantity (1 mmol) of 1-phenylacenaphthylene, a known compound, was reacted with ozone in 1.5 times the molar quantity of the compound in 15 ml of carbon tetrachloride at 0° C. Purification by silica gel column chromatography (eluent: benzene-hexane, 1:5) gave 149 mg of the desired compound (yield 54%). The physical properties of the product are shown in Table 1.

PREPARATION EXAMPLE 7
Preparation of 3,4-dihydro-1,3-diphenyl-1H-naphtho[1,8-de][1,2]oxazepin (Compound 7)

A 260 mg quantity (1 mmol) of 1-benzoyl-8-formylnaphthalene, a known compound, was reacted with 109 mg (equimolar quantity) of phenylhydroxylamine in 20 ml of ethanol at room temperature for 15 hours. The reaction mixture was poured into water, followed by extraction with ether and then by silica gel column chromatography for the separation of the product. Elution with benzene-hexane (1:1) gave 102 mg of the desired compound (yield 30%). The physical properties of the product are shown in Table 1.

PREPARATION EXAMPLE 8
Preparation of 1,2,4,5-tetrahydro-2,4,5-triphenyl-1,4-epoxy-3,2-benzoxazepin (Compound 8)

A 2.68 g quantity (10 mmols) of 1,2-diphenylindene, a known compound, was oxidized with ozone in 15 ml of methylene chloride, and the resulting reaction mixture was reduced with 2,77 g of triphenylphosphine in 30 ml of benzene at room temperature for 15 hours to obtain 1.8 g of 2-(α-benzoylbenzyl)benzaldehyde (yield 60%). A 300 mg portion (1 mmol) of the 2-(α-benzoylbenzyl)benzaldehyde was reacted with 109 mg of phenylhydroxylamine in 20 ml of ethanol at room temperature for 15 hours. The reaction mixture obtained was poured into water, followed by extraction with ether and then silica gel column chromatography for the separation of the product, consequently giving 117 mg of a 2:1 mixture of exo- and endo-isomers of the desired compound from a fraction obtained by elution with benzene-hexane (1:1) (yield 30%). The physical properties of the product are shown in Table 2.

PREPARATION EXAMPLE 9
Preparation of 4,5-dihydro-5-methyl-1-phenyl-1,4-epoxy-1H-2,3-benzodioxepin (Compound 9)

(1) A 1.03 g quantity (5 mmols) of 1-methyl-3-phenylindene, a known compound, was dissolved in 20 ml of carbon tetrachloride, and thereafter reacted with ozone in 1.3 times the molar quantity of the compound at 0° C. To the reaction mixture was added 50 ml of ether, and the organic layer was washed with saturated aqueous solution of sodium bicarbonate and then with saturated aqueous solution of sodium chloride. The organic layer obtained was dried over anhydrous magnesium sulfate, the solvent was thereafter distilled off in a vacuum, and the residue was subjected to silica gel column chromatography for separation and purification (eluent: benzene-hexane, 1:5), consequently giving 0.89 g (yield 70%) of a 2:1 mixture of exo- and endo-isomers of the desired compound. The two isomers were individually isolated by repeating column chromatography again and recrystallization from methanol. The physical properties of two isomeric products are shown in Table 1.

(2) The reaction was conducted on the same scale as above in 30 ml of methanol-methylene chloride (1:1) at 0° C., and the product was purified by silica gel column chromatography, affording 0.38 g of exo-isomer of the desired compound (yield 30%). The physical properties of the product are shown in Table 2.

PREPARATION EXAMPLE 10
Preparation of 4,5-dihydro-1,4,5-triphenyl-1,4-epoxy-1H-2,3-benzodioxepin (Compound 10)

A 344 mg quantity (1 mmol) of 1,2,3-triphenylindene, a known compound, was reacted with ozone in 1.5 times the molar quantity of the compound in 20 ml of carbon tetrachloride at 0° C. A fraction obtained by elution with benzene-hexane (1:5) was recrystallized from methanol, giving 196 mg of exo-isomer of the desired compound (yield 50%). The physical properties of the product are shown in Table 2.

PREPARATION EXAMPLE 11
Preparation of 4,5-dihydro-1,4-diphenyl-1,4-epoxy-1H-2,3-benzodioxepin (Compound 11)

A 268 mg quantity (1 mmol) of 2,3-diphenylindene, a known compound, was reacted with ozone in 1.5 times the molar quantity of the compound in 20 ml of carbon tetrachloride at 0° C. The reaction mixture was distilled to remove the solvent, and the residue was thereafter subjected to silica gel column chromatography for separation and purification, affording 221 mg of the desired compound (yield 70%). The physical properties of the product are shown in Table 2.

TABLE 1

| compd. No. | formula | Physical properties |
|---|---|---|
| 1 | | m. p. 178–180° C.<br>$^1$H-NMR(CDCl$_3$) δ: 1.42(s, 3H), 4.18(s, 1H), 6.7–7.3(m, 14H).<br>elementary analysis:<br>Calcd for C$_{22}$H$_{18}$O$_3$: C, 79.98; H, 5.49<br>Found: C, 79.76; H, 5.53 |
| 2 | | m. p. 139–141° C.<br>$^1$H-NMR(CDCl$_3$) δ: 1.21(d, J=7.0Hz, 3H), 2.44(s, 3H), 3.62 (q, J=7.0Hz, 1H), 6.8–7.6(m, 13H) |
| 3 | | m. p. 135–136° C.<br>$^1$H-NMR(CDCl$_3$) δ: 1.20(d, J=7.0Hz, 3H), 3.61(q, J=7.0Hz, 1H), 3.88(s, 3H), 6.8–7.6(m, 13H) |
| 4 | | m. p. 130–132° C.<br>$^1$H-NMR(CDCl$_3$) δ: 0.66(d, J=7.5Hz, 3H), 1.05(d, J=7.5Hz, 3H), 1.89(ddd, J=7.5, 7.5 and 2.0Hz, 1H), 3.45(d, J=2.0Hz, 1H), 6.7–7.3(m, 14 H).<br>elementary analysis:<br>Calcd for C$_{24}$H$_{22}$O$_3$: C, 80.42; H, 6.19.<br>Found: C, 80.19; H, 6.17. |

TABLE 1-continued

| compd. No. | formula | Physical properties |
|---|---|---|
| 5 | | m. p. 156–157° C.<br>$^1$H-NMR(CDCl$_3$) δ: 1.02(s, 9H), 4.12(s, 1H), 6.7–7.3(m, 14H).<br>elementary analysis:<br>Calcd for C$_{21}$H$_{24}$O$_3$: C, 80.61; H, 6.50.<br>Found: C, 80.63; H, 6.57. |
| 6 | | m. p. 130–131° C.<br>$^1$H-NMR(CDCl$_3$) δ: 6.78(s, 1H), 7.1–7.9(m, 11H).<br>elementary analysis:<br>Calcd for C$_{18}$H$_{12}$O$_3$: C, 78.25; H, 4.38.<br>Found: C, 78.20 ; H, 4.41. |
| 7 | | m. p. 147–148° C.<br>$^1$H-NMR(CDCl$_3$) δ: 6.26(s, 1H), 6.4–8.0(m, 16H)<br>$^{13}$C-NMR(CDCl$_3$) δ: 97.63, 108.17, 118.82–130.07 (21C), 151.12<br>IR spectrum (cm$^{-1}$): 1600, 1490, 1450, 1070, 960, 780, 725, 700. |

TABLE 2

| compd. No. | formula | physical properties |
|---|---|---|
| 8 | | m. p. 155–156° C.<br>$^1$H-NMR(CDCl$_3$) δ: 4.51(s, 1H), 6.18(s, endo)+6.32(s, exo) (1H; a 2:1 mixture), 7.1–8.0(m, 19H)<br>$^{13}$C-NMR(CDCl$_3$) δ: 55.14(exo), 57.61(endo), 96.49(exo), 96.54(endo), 109.48(endo), 110.03 (exo), 118.07–140.19(complex signals, exo + endo), 150.59(exo), 150.88(endo)<br>IR spectrum(cm$^{-1}$): 1595, 1485, 1450 |

TABLE 2-continued

| compd. No. | formula | physical properties |
|---|---|---|
| 9 | (structure) | exo-isomer<br>m. p. 127–128° C.<br>$^1$H-NMR(CDCl$_3$) δ: 1.46(d, J=7.5Hz, 3H), 3.12(q, J=7.5Hz, 1H), 5.96(brs, 1H), 6.9–7.6(m, 9H).<br>elementary analysis:<br>Calcd for C$_{16}$H$_{14}$O$_3$: C, 75.52; H, 5.55.<br>Found: C, 75.42; H, 5.42.<br>endo-isomer<br>m. p. 151–152° C.<br>$^1$H-NMR(CDCl$_3$) δ: 1.46(d, J=7.5Hz, 3H), 3.52 (qd, J=7.5 and 2.6Hz, 1H), 5.96(d, J=2.6Hz, 1H), 6.9–7.6(m, 9H).<br>elementary analysis:<br>Calcd for C$_{16}$H$_1$O$_3$: C, 75.52; H, 5.55.<br>Found: C, 75.48; H, 5.50. |
| 10 | (structure) | m. p. 171–173° C.<br>$^1$H-NMR(CDCl$_3$) δ: 4.63(s, 1H), 6.7–7.3(m, 19H).<br>elementary analysis:<br>Calcd for C$_{27}$H$_{20}$O$_3$: C, 82.63; H, 5.14.<br>Found: C, 82.34; H, 4.94. |
| 11 | (structure) | m. p. 119° C.<br>$^1$H-NMR(CDCl$_3$) δ: 3.60(d, J=17Hz, 1H), 3.83(d, J=17Hz, 1H), 6.8–7.9(m, 14H). |

EXAMPLE 1

Tablets

| | |
|---|---|
| Compound 6 | 100 g |
| Avicel [trademark, product of Asahi Chemical Industry Co., Ltd., crystalline cellulose] | 40 g |
| Corn starch | 30 g |
| Magnesium stearate | 2 g |
| TC-5 [trademark, product of Shin-Etsu Chemical Co., Ltd., hydroxypropylmethyl cellulose] | 10 g |
| Polyethylene glycol-6000 | 3 g |
| Caster oil | 40 g |
| Ethanol | 40 g |

Compound 6, Avicel, corn starch and magnesium stearate were mixed together, ground and punched using a pestle of sugar coating R=10 mm. The tablets obtained were coated with a film coating agent comprising TC-5, polyethylene glycol-6000, castor oil and ethanol to prepare film-coated tables of the above composition.

EXAMPLE 2

Ointment

| | |
|---|---|
| Compound 7 | 2 g |
| Purified lanolin | 5 g |
| Bleached beeswax | 5 g |
| White petrolatum | 88 g |
| Total quantity | 100 g |

Bleached beeswax was liquefied by heating, compound 7, purified lanolin and white petrolatum were then added to the liquid, and the mixture was heated until a liquid was obtained and thereafter stirred until the liquid mixture started to solidify, whereby an ointment of above composition was prepared.

EXAMPLE 3

Suppositories

| | |
|---|---|
| Compound 8 | 50 mg |
| Witepsol W-35 [trademark, product of Dynamite Nobel Foundation, a mixture of mono-, di- and tri-glycerides of saturated fatty acids, i.e., lauric to stearic acids] | 1400 mg |

The above composition was made into suppositories by the usual method.

TEST EXAMPLE 1

Urokinase Production Inhibition Test

This test was conducted substantially according to the method described in Biochem. Biophys. Res. Commun., 142(1), 147–54(1987) as will be described in detail below.

<Preparation of Cells>

Human fibrosarcoma cells HT-1080 were purchased from American Type Culture Collection (product of Rockville). HT-1080 cells were cultured at 37° C. in a 5% $CO_2$ incubator in RPMI-1640 medium (product of Nissui Seiyaku Co., Ltd.) containing 10% (v/v) of immobilized bovine fetal serum (product of ATLANTA Biological). The cells were suspended in 0.2% trypsin 2 mM EDTA solution for use in the experiment.

<Experimental Method and Result>

The suspension of HT-1080 cells as adjusted to $1 \times 10^5$ cells/ml was placed onto a 96-well flat-bottomed incubation plate dividedly in 200 µl quantities ($2 \times 10^4$ cells/well) and incubated at 37° C. for 4 hours. The supernatant was thereafter removed and replaced with the same amount of serum-free medium [hereinafter referred to as "serum(−)"], followed by incubation for 20 hours. Subsequently, serum (−) was replaced with 199 µl of serum-containing medium [hereinafter referred to as "serum(+)"], and 1 µl of a sample solution containing an active component of the invention and prepared by dissolving the component in dimethyl sulfoxide (DMSO) was added to serum(+) in the incubation plate, followed by further incubation at 37° C. for 24 hours. The resulting supernatant was removed under suction, serum (−) was added in 200 µl quantities, followed by incubation again for 24 hours, and the supernatant of the culture was collected.

To determine the conditions for measuring urokinase activity in the supernatant, the reaction time and the concentration of a synthetic substrate were investigated using recombinant human urokinase (product of CHROMOGENIX AB) and VLKpA (valylleucyllysyl p-nitroamide, product of Sigma Chemical CO.) serving as the synthetic medium at a constant concentration (2.8 µg/ml) of plasminogen. When the culture supernatant of HT-1080 cells was checked for urokinase activity preliminarily, the activity was about 0.02 IU/µl. An urokinase solution with activity of 0.02 IU/µl was reacted with the synthetic substrate of varying concentrations. It was found that the urokinase activity increased concentration-dependently up to a substrate concentration of 10 mM. Next, the reaction was found to be dependent on the reaction time. In view of these results, the urokinase activity was determined by the following experiment under the conditions of 10 mM in synthetic substrate concentration and 30 minutes in reaction time.

A 85 µl portion of the culture supernatant and 15 µl of substrate reaction mixture [427 mM Tris-HCl (pH 8.0), 27 mM EDTA (pH 8.0), 1.5 mM VLKpA, 125 µg/ml plasminogen (product of CHROMOGENIX AB] were mixed together in a 96-well incubation plate and reacted at 37° C. for 30 minutes, and the reaction mixture was checked for absorbance at 405 nm using an immunoreader. The urokinase production inhibition ratio was calculated from the following equation.

$$\text{Inhibition ratio (\%)} = (1 - T/C) \times 100$$

wherein T is the average absorbance of a group given the sample, and C is the average absorbance of a control group. Table 3 shows the result.

TABLE 3

| Compound No. | concentration (µg/ml) | urokinase inhibition ratio (%) |
|---|---|---|
| 1 | 3.13 | 90.5 |
|   | 1.56 | 90.0 |
| 2 | 12.5 | 88.3 |
| 3 | 6.25 | 94.4 |
|   | 3.13 | 93.8 |
| 6 | 50.0 | 90.1 |
| 7 | 25.0 | 94.8 |
|   | 12.5 | 93.1 |
| 8 | 50.0 | 93.4 |
|   | 25.0 | 82.2 |
| 10 | 3.13 | 94.1 |
| 11 | 3.13 | 91.4 |

EXPERIMENTAL EXAMPLE 2

Angiogenesis Inhibition Test

This experiment was conducted substantially according to the fertilized egg chorioallantonic membrane (abbreviated as CAM) method described in ADVANCES IN CANCER RESEARCH, vol. 43, 175–203. The fertilized hen's eggs (Plymouth Rock breed×white leghorn breed) used were purchased from Gotoh Brooder (Gifu Prefecture) and incubated in an incubator (product of Tokyo Rikagaku Kikai Co., Ltd.) at a humidity of 70% and 37° C.

The air chamber of each egg was located by illuminating the egg and the egg shell was injured with a rotary file at two locations, i.e., an upper portion of the air chamber and a side portion of the egg on day 3, taking the day when the incubation was started as day 0. About 3 ml of the albumen was aspirated through the side hole with a syringe for removal, and the air was removed from the upper portion with a dropper. With the side hole sealed with OpSite (product of Smith and Nephew Ltd.), the air chamber upper portion was injured in the form of a 1 cm square, the egg shell and the egg membrane were removed from the square area, and the opening was sealed with OpSite. The seal was removed from the opening on day 5 to form a window, which was sealed with Tegaderm (product of 3M Health Care Ltd.). A disk is made from 20 µl of 1% gelatin with drying, 20 µl of 0.5% aqueous methyl cellulose solution containing an active component of the invention was applied to the disk to form a superposed layer, and the resulting disk was dried in a clean bench. The Tegaderm seal was removed, the disk was placed at rest on the CAM, and the window was sealed again. The shell was removed from an upper portion of the egg on day 7, and 1 ml of 20% Intralipos (product of Green Cross Co., Ltd.) was injected into the egg under the CAM. The CAM was observed under a surgical microscope and photographed at a magnification of ×4 to ×8.

The effect to inhibit angiogenesis was determined substantially according to the method described in Cancer Lett., 48(2), 157–62(1989). More specifically, a vessel-free region, when found over a distance of at least 2 mm around the methyl cellulose layer, was interpreted as indicating angiogenesis inhibitory activity (+), weak inhibitory activity of less than 2 mm as indicating quasi-positive (±), and no vessel-free region within 2 mm as indicating negative (−). At least six fertilized eggs were used for testing. The angiogenesis inhibition ratio was determined by evaluating (+) as 1 point, (±) as 0.5 point and (−) as 0 point, and calculating the ratio of the points each compound scored for all the eggs used. Table 4 shows the result.

TABLE 4

| Compound No. | dosage (μg/egg) | angiogenesis inhibition ratio (%) |
| --- | --- | --- |
| 1 | 40 | 75 |
|   | 10 | 67 |
| 3 | 40 | 63 |
| 6 | 40 | 100 |
| 8 | 40 | 56 |

TEST EXAMPLE 3

Test for Inhibition of Metastasis to Lung and Inhibition of Growth of Primary Tumor The test animals used were 7-week-old female C57BL/6 mice (Nippon Charles River) weighing 17 to 20 g. A subcutaneous tumor ($1.0 \times 10^5$ cells) of Lewis lung cancer strain (LLC) was transplanted in the mice, and a suspension of a test compound in an aqueous solution of 3% ethanol and 5% gum arabic was given on day 3 and thereafter. The test compound used was compound 6, which was intraperitoneally administered at a dose of 15 mg/kg every other day. On the other hand, 100 μl of 3% ethanol-5% gum arabic aqueous solution was intraperitoneally given to a control group. The mice were checked for body weight and the major and minor diameters of the primary tumor every other day, and an estimated tumor volume (V) was determined by calculating (minor diameter)$^2$×(major diameter)÷2. The tumor growth inhibition ratio (%) was calculated from the estimated tumor volume of day 24 after the transplantation using the following equation.

Tumor growth inhibition ratio (%)=(1−Tv/Cv)×100 wherein Tv is the tumor volume (mm$^3$) of the group given the test compound, and Cv is the tumor volume (mm$^3$) of the control group.

The tumor was excised from each mouse, fixed with acetone, and checked for the number of lesions metastasized to the lungs to calculate the lung metastasis inhibition ratio (%) from the following equation.

Lung metastasis inhibition ratio (%)=(1−T/C)×100 wherein T is the number of metastatic nodules in the group given the test compound, and C is the number of metastatic nodules in the control group.

Consequently, the tumor growth inhibition ratio achieved in the group given compound 6 was 59.2%, and the lung metastasis inhibition ratio in this group was 75.8%, hence a significant inhibitory effect on both the primary tumor and metastasis. The treatment entailed no death in the mice and little or no reduction in body weight.

The results given above reveal that the active component of the invention is reduced in toxicity and highly effective for inhibiting the metastasis of tumors and the growth of tumors.

INDUSTRIAL APPLICABILITY

As stated above, the medicinal comprising as an active component an ozonide derivative represented by the formula (1) has high activity to inhibit production of urokinase and is useful as a urokinase production inhibitor. The medicinal of the invention also has high angiogenesis inhibitory activity and is therefore useful as an agent for treating or preventing diseases accompanying angiogenesis. The diseases accompanying angiogenesis include, for example, malignant tumors, metastases of tumors, benign tumors (e.g., hemangioma, acoustic neurinoma, neurofibroma, trachoma and pyogenic granuloma), vascular dysfunction, inflammation and immune disorders, Behcet's syndrome, gout, arthritis, chronic articular rheumatism, psoriasis, diabetic retinopathy and other diseases originating in ocular blood vessels (e.g., fibroplasia of the posterior lens, macular degeneration, rejection of corneal transplant and angiogenesis glaucoma), osteoporosis, etc.

What is claimed is:

1. A urokinase production inhibitor comprising as an active component an ozonide compound of formula (1)

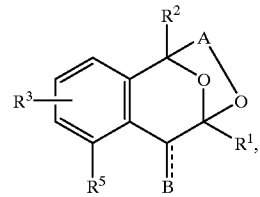

(1)

wherein

A is an oxygen atom or N—R wherein R is phenyl or phenyl having as a substituent lower alkyl having 1 to 6 carbon atoms, lower alkoxyl having 1 to 6 carbon atoms or a halogen atom;

B is an oxo group or —R$^4$; and a) when A is an oxygen atom, R$^1$ is a hydrogen atom, lower alkyl having 1 to 6 carbon atoms, phenyl or phenyl having as a substituent lower alkyl having 1 to 6 carbon atoms, lower alkoxyl having 1 to 6 carbon atoms, lower alkoxycarbonyl having 2 to 7 carbon atoms or a halogen atom, R$^2$ is phenyl or phenyl having as a substituent lower alkyl having 1 to 6 carbon atoms, lower alkoxyl having 1 to 6 carbon atoms or a halogen atom, R$^3$ is a hydrogen atom, lower alkyl having 1 to 6 carbon atoms, lower alkoxyl having 1 to 6 carbon atoms or a halogen atom, B is an oxo group or —R$^4$, R$^4$ is a hydrogen atom, lower alkyl having 1 to 6 carbon atoms, a halogen atom, lower alkanoyl having 2 to 6 carbon atoms or phenyl, and R$^5$ is a hydrogen atom, lower alkyl having 1 to 6 carbon atoms, lower alkoxyl having 1 to 6 carbon atoms or a halogen atom or forms an aromatic 6-membered ring when combined with R$^4$; or b) when A is N—R, R$^1$ is a hydrogen atom, lower alkyl having 1 to 6 carbon atoms, phenyl or phenyl having as a substituent lower alkyl having 1 to 6 carbon atoms, lower alkoxyl having 1 to 6 carbon atoms, or a halogen atom, R$^2$ is a hydrogen atom or lower alkyl having 1 to 6 carbon atoms, R$^3$ is a hydrogen atom, lower alkyl having 1 to 6 carbon atoms, lower alkoxyl having 1 to 6 carbon atoms or a halogen atom, B is —R$^4$, wherein R$^4$ is a hydrogen atom, phenyl or phenyl having as a substituent lower alkyl having 1 to 6 carbon atoms, lower alkoxyl having 1 to 6 carbon atoms or a halogen atom, and $R^5$ is a hydrogen atom, lower alkyl having 1 to 6 carbon atoms, lower alkoxyl having 1 to 6 carbon atoms or a halogen atom or forms an aromatic 6-membered ring when combined with $R^4$.

2. The urokinase production inhibitor as defined in claim 1, wherein A is an oxygen atom, $R^1$ is a hydrogen atom, methyl, ethyl, phenyl or phenyl having as a substituent methyl, methoxy, methoxycarbonyl or a chlorine atom, $R^2$ is phenyl or phenyl having as a substituent methyl, methoxy or a chlorine atom, $R^3$ is a hydrogen atom, $R^4$ is a hydrogen atom, methyl, ethyl, isopropyl, tert-butyl, a chlorine atom, oxo, acetyl or phenyl, and $R^5$ is a hydrogen atom.

3. The urokinase production inhibitor as defined in claim 2, wherein A is a oxygen atom, $R^1$ is a hydrogen atom, methyl or phenyl, $R^2$ is phenyl or phenyl having methoxy as a substituent, $R^3$ is a hydrogen atom, $R^4$ is a hydrogen atom, methyl, isopropyl or phenyl, and $R^5$ is a hydrogen atom.

4. The urokinase production inhibitor as defined in claim 1, wherein A is an oxygen atom, $R^1$ is a hydrogen atom or phenyl, $R^2$ is phenyl, $R^3$ is a hydrogen atom, and $R^5$ is combined with $R^4$ to form a phenyl ring.

5. The urokinase production inhibitor as defined in claim 1, wherein A is N—R, R is phenyl, $R^1$ is a hydrogen atom or phenyl, $R^2$ is a hydrogen atom, $R^3$ is a hydrogen atom, $R^4$ is a hydrogen atom or phenyl, and $R^5$ is a hydrogen atom.

6. The urokinase production inhibitor as defined in claim 1, wherein A is N—R, R is phenyl, $R^1$ is a hydrogen atom or phenyl, $R^2$ is a hydrogen atom, $R^3$ is a hydrogen atom, and $R^5$ is combined with $R^4$ to form a phenyl ring.

7. An angiogenesis inhibitor comprising as an active component an ozonide compound of formula (1)

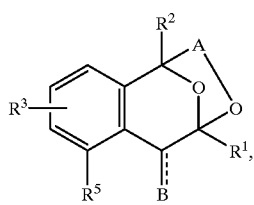

(1)

wherein

A is an oxygen atom or N—R, wherein R is phenyl or phenyl having as a substituent lower alkyl having 1 to 6 carbon atoms, lower alkoxyl having 1 to 6 carbon atoms or a halogen atom;

B is an oxo group or —$R^4$; and a) when A is an oxygen atom, $R^1$ is a hydrogen atom, lower alkyl having 1 to 6 carbon atoms, phenyl or phenyl having as a substituent lower alkyl having 1 to 6 carbon atoms, lower alkoxyl having 1 to 6 carbon atoms, lower alkoxycarbonyl having 2 to 7 carbon atoms or a halogen atom, $R^2$ is phenyl or phenyl having as a substituent lower alkyl having 1 to 6 carbon atoms, lower alkoxyl having 1 to 6 carbon atoms or a halogen atom, $R^3$ is a hydrogen atom, lower alkyl having 1 to 6 carbon atoms, lower alkoxyl having 1 to 6 carbon atoms or a halogen atom, B is an oxo group or —$R^4$, wherein $R^4$ is a hydrogen atom, lower alkyl having 1 to 6 carbon atoms, a halogen atom, lower alkanoyl having 2 to 6 carbon atoms or phenyl, and $R^5$ is a hydrogen atom, lower alkyl having 1 to 6 carbon atoms, lower alkoxyl having 1 to 6 carbon atoms or a halogen atom or forms an aromatic 6-membered ring when combined with $R^4$; or b) when A is N—R, $R^1$ is a hydrogen atom, lower alkyl having 1 to 6 carbon atoms, phenyl or phenyl having as a substitutent lower alkyl having 1 to 6 carbon atoms, lower alkoxyl having 1 to 6 carbon atoms or a halogen atom, $R^2$ is a hydrogen atom or lower alkyl having 1 to 6 carbon atoms, $R^3$ is a hydrogen atom, lower alkyl having 1 to 6 carbon atoms, lower alkoxyl having 1 to 6 carbon atoms or a halogen atom, B is —$R^4$, wherein $R^4$ is a hydrogen atom, phenyl or phenyl having as a substituent lower alkyl having 1 to 6 carbon atoms, lower alkoxyl having 1 to 6 carbon atoms or a halogen atom, and $R^5$ is a hydrogen atom, lower alkyl having 1 to 6 carbon atoms, lower alkoxyl having 1 to 6 carbon atoms or a halogen atom or forms an aromatic 6-membered ring when combined with $R^4$.

8. The angiogenesis inhibitor as defined in claim 7, wherein A is an oxygen atom, $R^1$ is a hydrogen atom, methyl, ethyl, phenyl or phenyl having as a substituent methyl, methoxy, methoxycarbonyl or a chlorine atom, $R^2$ is phenyl or phenyl having as a substituent methyl, methoxy or a chlorine atom, $R^3$ is a hydrogen atom, $R^4$ is a hydrogen atom, methyl, ethyl, isopropyl, tert-butyl, a chlorine atom, oxo, acetyl or phenyl, and $R^5$ is a hydrogen atom.

9. The angiogenesis inhibitor as defined in claim 8, wherein A is an oxygen atom, $R^1$ is a hydrogen atom, methyl, or phenyl, $R^2$ is phenyl or phenyl having methoxy as a substituent, $R^3$ is a hydrogen atom, $R^4$ is a hydrogen atom, methyl, isopropyl or phenyl, and $R^5$ is a hydrogen atom.

10. The angiogenesis inhibitor as defined in claim 7, wherein A is an oxygen atom, $R^1$ is a hydrogen atom or phenyl, $R^2$ is phenyl, $R^3$ is a hydrogen atom, and $R^5$ is combined with $R^4$ to form a phenyl ring.

11. The angiogenesis inhibitor as defined in claim 7, wherein A is N—R, R is phenyl, $R^1$ is a hydrogen atom or phenyl, $R^2$ is a hydrogen atom, $R^3$ is a hydrogen atom, $R^4$ is a hydrogen atom or phenyl, and $R^5$ is a hydrogen.

12. The angiogenesis inhibitor as defined in claim 7, wherein A is N-R, R is phenyl, $R^1$ is a hydrogen atom or phenyl, $R^2$ is a hydrogen atom, $R^3$ is a hydrogen atom, and $R^5$ is combined with $R^4$ to form a phenyl ring.

13. A method of inhibiting production of urokinase by administering to a human, a urokinase production inhibitory effective amount of an ozonide compound of formula (1) according to claim 1.

14. A method of treating a disease accompanying angiogenesis by administering to a human, an angiogenesis inhibitory effective amount of an ozonide compound of formula (1) according to claim 1.

15. A pharmaceutical composition suitable for inhibiting urokinase production comprising a urokinase production inhibitory effective amount of a compound of claim 1, and a pharmaceutically acceptable carrier.

16. A pharmaceutical composition suitable for inhibiting angiogenesis comprising an angiogenesis inhibitory effective amount of a compound of claim 1, and a pharmaceutically acceptable carrier.

* * * * *